US006982061B1

(12) United States Patent
Brashear

(10) Patent No.: US 6,982,061 B1
(45) Date of Patent: Jan. 3, 2006

(54) SYSTEM AND METHOD FOR ODORIZING A GAS LINE

(75) Inventor: Brian Brashear, Mont Belvieu, TX (US)

(73) Assignee: Natural Gas Odorizing, Inc., Baytown, TX (US)

( * ) Notice: Subject to any disclaimer, the term of this patent is extended or adjusted under 35 U.S.C. 154(b) by 579 days.

(21) Appl. No.: 10/205,269

(22) Filed: Jul. 25, 2002

(51) Int. Cl.
*A61L 2/00* (2006.01)

(52) U.S. Cl. .................. 422/5; 422/4; 222/3; 222/187; 137/587; 141/18; 141/197

(58) Field of Classification Search .................... 422/5; 222/4, 187; 137/171, 587, 564.5, 205.5; 261/64.1, 64.3; 48/195; 141/18, 94, 82, 141/197
See application file for complete search history.

(56) References Cited

U.S. PATENT DOCUMENTS 1,771,315 A * 7/1930 Remfry ......................... 303/1
3,194,444 A * 7/1965 Hubert .................... 137/205.5
3,568,405 A * 3/1971 Perry ......................... 210/675
3,907,515 A * 9/1975 Mulliner ...................... 48/195
4,504,281 A * 3/1985 Williams et al. .............. 48/195
4,611,294 A * 9/1986 Stanfill ........................ 700/68
4,941,616 A * 7/1990 Liebler ....................... 239/310

OTHER PUBLICATIONS

*Mini Mist Remover*, http://www.halfdiamond6t.com/tline/mini_mist_remover.htm.
*Odorant Equipment*; http://www.halfdiamond6t.com/tline/equipment.htm.
*Odorizer Model*; http://www.halfdiamond6t.com/tline/odorizer_model.htm.
*Typical Installation of Natural Gas Odorizers*; http://www.halfdiamond6t.com/tline/typical%20installation.htm.
*Small Tap Odorizers*; http://www.halfdiamond6t.com/tline/small%20tap.htm.

* cited by examiner

*Primary Examiner*—John Kim
*Assistant Examiner*—Brad Y. Chin
(74) *Attorney, Agent, or Firm*—Ruben C. DeLeon; Winstead Sechrest & Minick

(57) ABSTRACT

A closed system odorant chamber or wick-style odorizer and method for transferring odorant to an odorant chamber is described. Two cylinders are connected to the odorant chamber, which in turn may be connected to a gas line. The pressure differential between the two cylinders causes odorant to flow into the odorant chamber until an appropriate odorant level is reached. After filling up the odorant chamber, the two cylinders are disconnected from the odorant chamber. It is emphasized that this abstract is provided to comply with the rules requiring an abstract that will allow a searcher or other reader to quickly ascertain the subject matter of the technical disclosure; and is submitted with the understanding that it will not be used to interpret or limit the scope or meaning of the claims under 37 C.F.R. § 1.72.

8 Claims, 2 Drawing Sheets

SYSTEM AND METHOD FOR ODORIZING A GAS LINE

FIELD OF THE INVENTION

The invention relates generally to natural gas processing, and more particularly to an apparatus and method for transferring, in a closed system, odorant to an odorant chamber while the apparatus continues to odorize natural gas.

BACKGROUND OF THE INVENTION

Natural gas is odorless. For safety reasons, odorant must be added to natural gas in order to detect leaks in natural gas systems. Typically, odorant is transferred from an odorant storage chamber to natural gas flowing in a gas line. To accomplish this, several odorization systems are available. One type of odorization system is a farm tap or wick-style odorizer.

Farm taps are small inline odorization systems that are usually composed of an odorant chamber connected to a gas line by a fitting. Typically, a cotton wick is inserted through the fitting such that the majority of the wick is located in the odorant chamber, with the remaining smaller portion of the wick being exposed to the natural gas stream in the gas line. In the odorant chamber, the wick contacts and becomes saturated with the odorant. By capillary action, the odorant travels up the wick and then is vaporized into the natural gas stream in the gas line, resulting in odorized natural gas downstream of the odorizer.

Currently, farm taps require the owner or operator to physically pour odorant into the odorant chamber. This is usually accomplished by disconnecting the odorant chamber from the gas line and pouring the odorant through the opening to which the fitting is attached during odorizer operation. If the farm tap or wick-style odorizer is equipped with a second opening in addition to the opening at the connection between the chamber and the gas line, odorant may also be poured into the odorant chamber by unplugging the second opening and pouring the odorant in through the second opening.

Regardless of how pouring is accomplished, at least three problems exist with regard to the current practice of pouring odorant into the odorant chamber. First, pouring usually results in a sufficient amount of odor being released into the surrounding environment, creating nuisance and exposure problems for nearby residences or businesses. A second problem is that the set-up and physical pouring of the odorant is not time efficient. A third problem is that the odorant chamber is typically disconnected from the gas line during odorant pouring, temporarily halting natural gas odorization. This third problem is typical in farm tap styles where the pouring in of odorant requires the removal of the odorant chamber from the gas line.

Therefore, what is needed is an apparatus and method that allows odorant to be transferred to an odorant chamber without exposing odorant to the environment and creating a nuisance, wasting field personnel work time, and interrupting natural gas odorization.

SUMMARY OF THE INVENTION

The present invention provides an apparatus and method for transferring natural gas odorant to an odorant chamber in a closed system while continuing to odorize natural gas. Two odorant cylinders are connected to an odorant chamber, which in turn may be connected to a gas line. One odorant cylinder is initially filled with odorant while the other odorant cylinder is initially empty. The pressure differential between the two additional odorant cylinders causes the odorant to flow into the odorant chamber until an appropriate odorant level is reached. The initially empty odorant cylinder is vented to the atmosphere in conjunction with a filter to prevent any nuisance-creating odors from entering the surrounding environment. After filling up the odorant chamber, the two additional odorant cylinders are disconnected from the odorant chamber. Consequently, odorant transfer is accomplished without exposing the odorant to the surrounding environment and without interrupting the odorization of natural gas in the gas line.

Therefore, in accordance with the previous summary, objects, features, and advantages of the present invention will become apparent to one skilled in the art from the subsequent description and the appended claims taken in conjunction with the accompanying drawings.

BRIEF DESCRIPTION OF THE DRAWINGS

To illustrate the manner in which the advantages and features of the invention are obtained, a more particular description of the invention will be given with reference to the attached drawings. These drawings only illustrate selected aspects of the invention and thus do not limit the invention's scope. In the drawings.

DETAILED DESCRIPTION

Figure 1:
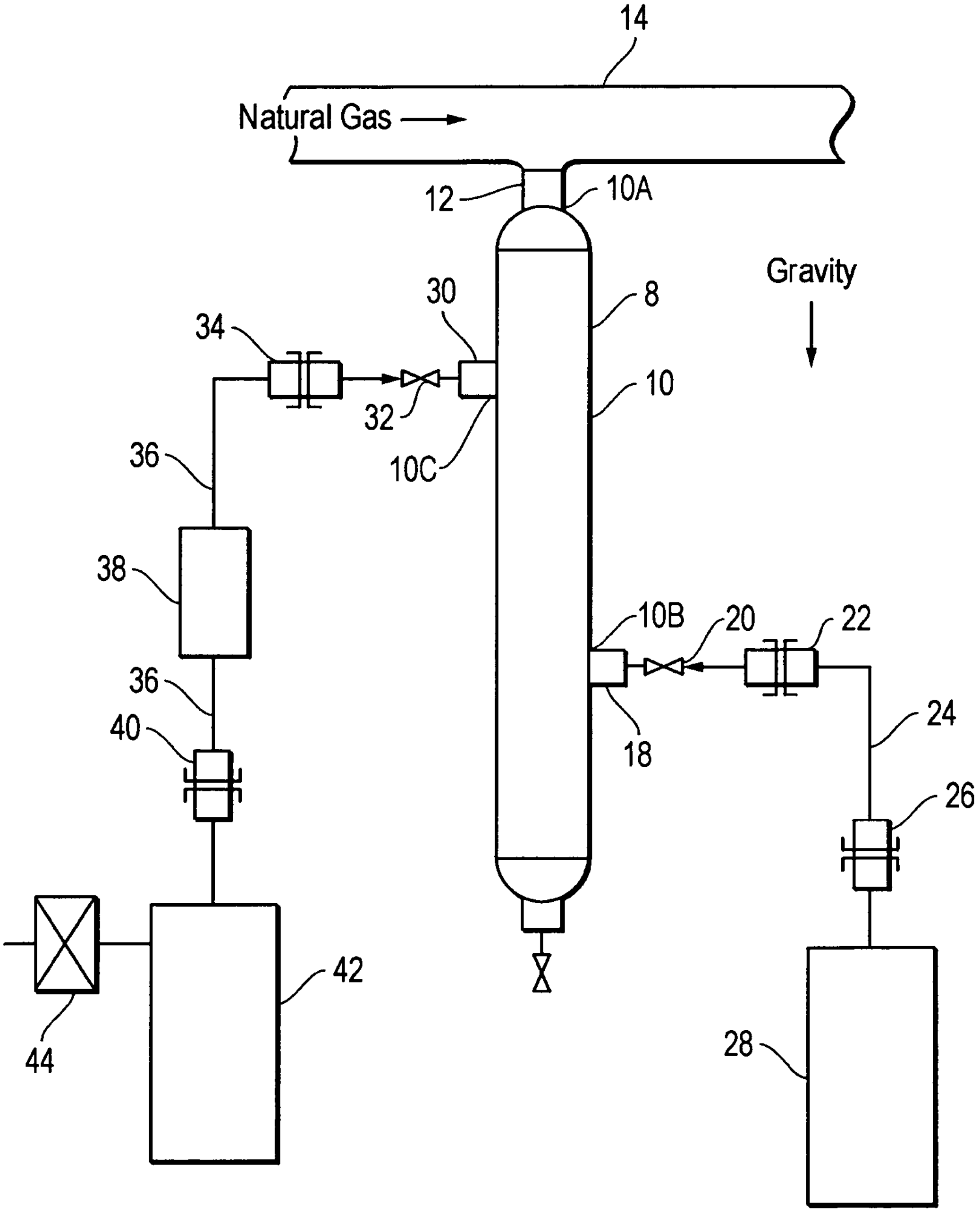
FIG. 1 is a diagram illustrating an example of one embodiment according to the present invention.

The components of one embodiment of the present invention and their corresponding reference numerals in the drawings will first be described and then the details of the embodiment in operation will be described. Specific examples are given to illustrate aspects of the invention, but those of skill in the art will understand that other examples may also fall within the meaning of the terms used.

Referring to FIG. 1, the components of a farm tap or wick-style odorizer 8 are described. The reference numeral 10 refers, in general, to an odorant chamber, tank, or other storage device, which is also the main body of the farm tap 8, and having the openings 10*a*, 10*b*, and 10*c*. A fitting 12, such as a nipple, is used to connect a gas line 14 to the odorant chamber 10.

Figure 2:
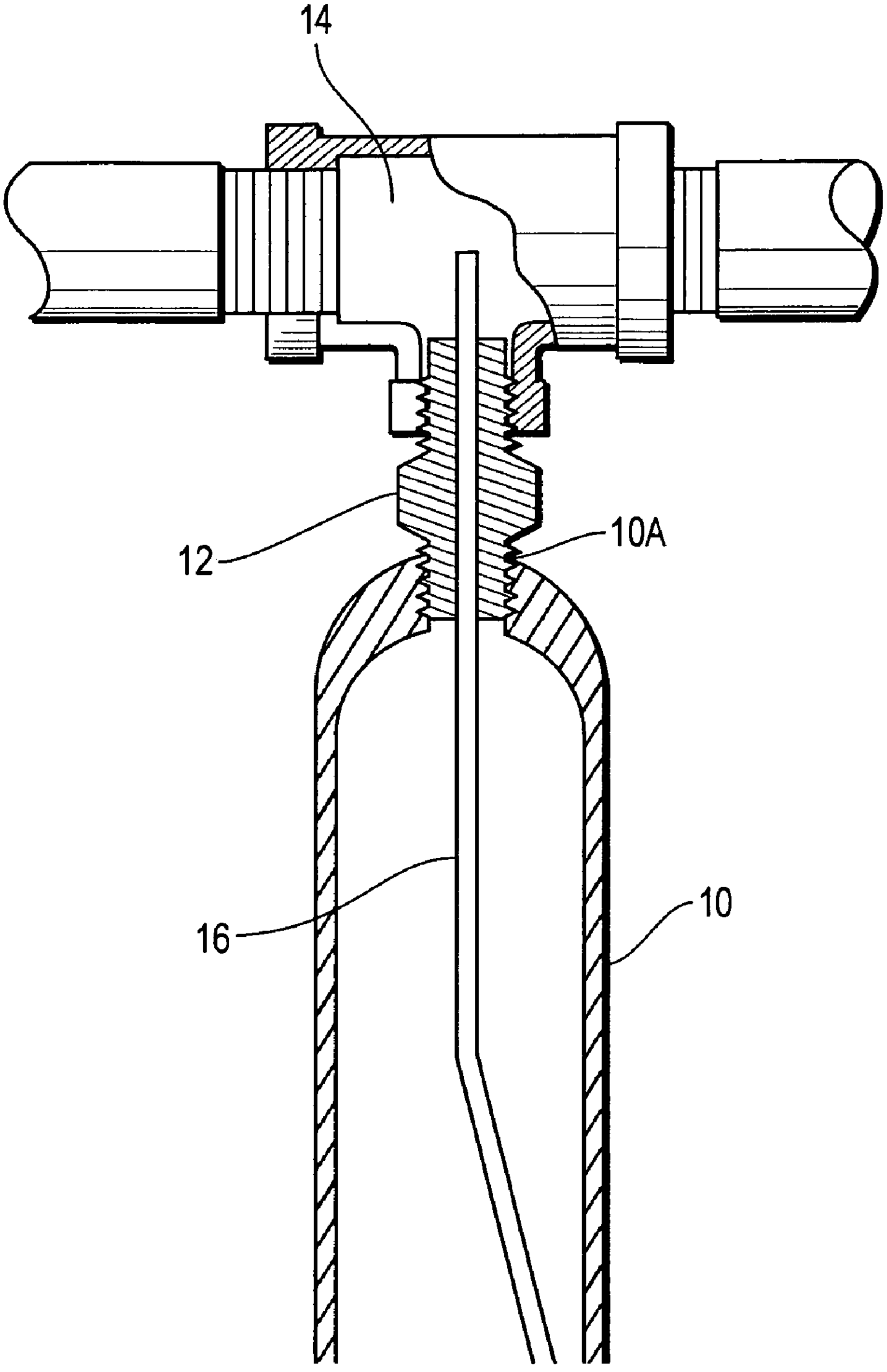
FIG. 2 is a side, cut-away view illustrating the interface between the odorant chamber, nipple fitting, wick, and gas line of FIG. 1.

Referring now to FIG. 2, the inner components of the farm tap 8 are described. A wick 16 is connected to the fitting 12 with the opposite ends of the wick protruding into the inner portion of the odorant chamber 10 and the inner portion of the gas line 14, respectively.

Referring back to FIG. 1, the components used to supply odorant to the farm tap 8 are described. A fitting 18, such as a coupling, is used to connect an inlet valve 20 to the opening 10*b*. A connector 22, such as a dripless quick disconnect connector, is used to connect an odorant line 24 to the inlet valve 20 in this embodiment. A connector 26, such as a dripless quick disconnect connector, is used to connect a pressurized source cylinder 28, which is initially filled with odorant, to the odorant line 24.

Next, the components used to transfer excess odorant out of the farm tap 8 are described. A fitting 30, such as a coupling, is used to connect an outlet valve 32 to the opening 10*c*. A connector 34, such as a dripless quick disconnect connector, is used to connect an odorant line 36 to the outlet valve 32. A flow meter 38 is connected inline with the odorant line 36. A connector 40, such as a dripless quick disconnect connector, is used to connect an excess cylinder 42, which is initially empty of odorant, to the odorant line 36. A charcoal filter 44 is connected to the excess cylinder 42.

In operation, the farm tap is first connected to the gas line 14. The inlet valve 20 and the outlet valve 32 are connected to the openings 10*b* and 10*c*, respectively. The inlet valve 20 and the outlet valve 32 are initially both in the "closed" position. The odorant chamber 10, initially empty of odorant, is connected to the gas line 14 perpendicularly. The odorant chamber 10 is oriented such that, when the odorant chamber 10 is filled, the odorant will move up the wick, substantially in the opposite direction of gravity. This orientation also results in the opening 10*c* being at a higher elevation than the opening 10*b*, with respect to the ground level.

When the farm tap 8 is empty or close to being empty, the components used to fill the odorant chamber 10 with odorant may be assembled. The pressurized source cylinder 28, initially filled with odorant, is positioned at a convenient location in relation to the odorant chamber 10. Using the connectors 22 and 26, the odorant line 24 is connected to the inlet valve 20 and the pressurized source cylinder 28, respectively.

In like manner, the excess cylinder 42, initially empty of odorant, is positioned at a convenient location in relation to the odorant chamber 10. Using the connectors 34 and 40, the odorant line 36, with the flow meter 38 connected inline with the odorant line 36, is connected to the outlet valve 32 and the excess cylinder 42, respectively. If not already connected, the charcoal filter 44 is then connected to the excess cylinder 42.

After the above connections have been made, the charcoal filter 44 and the excess cylinder 42 are configured such that there exists a vent path from the excess cylinder 42, through the charcoal filter 44, and out to the atmosphere. The pressurized source cylinder 28 is configured such that, when subjected to a pressure differential, odorant is able to flow out of the pressurized source cylinder 28, through the odorant line 24, and into the odorant chamber 10.

To create a pressure differential in the apparatus, the outlet valve 32 is first adjusted from the "closed" to the "open" position. Next, the inlet valve 20 is adjusted from the "closed" to the "open" position. At this point in time, the pressure difference between the pressurized source cylinder 28 and the atmosphere results in the odorant flowing from the pressurized source cylinder 28 to the odorant chamber 10 through the opening 10*b*. The odorant level in the odorant chamber 10 rises, filling the odorant chamber 10 until the odorant level reaches the opening 10*c*. At this point, the odorant level substantially ceases to rise towards the opening 10*a*, instead flowing out of the odorant chamber 10 through the opening 10*c*. The odorant flows through the odorant line 36, resulting in the flow meter 38 indicating that the odorant is flowing through the odorant line 36. This indication by the flow meter 38 signals that the odorant chamber 10 is adequately filled up with the odorant. At this point, the inlet valve 20 is then adjusted from the "open" to the "closed" position, preventing the odorant from flowing into the odorant chamber 10. The outlet valve 32 is then adjusted from the "open" to the "closed" position, resulting in the odorant chamber 10 being non-pressurized and filled with the odorant.

The excess odorant that travels through the odorant line 36 collects in the excess cylinder 42. This excess cylinder 42 is vented to the atmosphere, with the charcoal filter 44 serving to prevent odor from entering into the atmosphere.

After the odorant chamber 10 is filled with odorant, the odorant lines 24 and 36, the source cylinder 28, and the excess cylinder 42 may be removed from the vicinity of the odorant chamber 10 using the connectors 22, 26, 34, and 40, respectively. The use of dripless quick disconnect connectors to connect the aforementioned components is recommended to prevent any odorant from entering the surrounding environment or atmosphere during apparatus assembly or disassembly.

Several advantages result from the present invention. For one, the invention is a closed system so there is no pouring of odorant from any container into the odorant chamber 10. This results in the odorant never being directly exposed to the surrounding environment, preventing nuisance and exposure problems. Also, not having to physically pour odorant significantly reduces the time required to fill the odorant chamber 10. By using the pressure differential between the pressurized source cylinder 28 and the atmosphere, the time required to fill the odorant chamber 10 using the present invention is substantially less than the time required to pour odorant into the odorant chamber 10. Additionally, the present invention does not interrupt the odorization of the natural gas stream in the gas line 14. Since the odorant chamber 10 remains connected to the gas line, odorant may continue to travel up the wick 16 and into the gas line 14 before, during, and after the filling up of the odorant chamber 10 with odorant.

It is understood that several variations may be made in the foregoing without departing from the scope of the invention. For example, many different types of containers suitable for storing gas or odorant and rated at an acceptable pressure rating may be used instead of the odorant chamber 10, the pressurized source cylinder 28, or the excess cylinder 42. Also, the number of connectors used in conjunction with the odorant lines 24 and 36 may be varied. Although the above-described embodiment uses two connectors with each of the odorant lines 24 or 36, this number could be reduced to one connector per odorant line, with the odorant lines 24 and 36 being attached to the pressurized source cylinder 28 and the excess cylinder 42, respectively, throughout the operation of the invention. Also, the odorant lines 24 and 36 may not be used at all, instead using another type of connection arrangement between the pressurized source cylinder 28 and the inlet valve 22, and the excess cylinder 42 and the outlet valve 32, respectively. Also, any type of valve may be used for either the inlet valve 22 or the outlet valve 32, such as a ball or needle valve. In addition, any type of flow meter may be used for the flow meter 38, such as a digital, mechanical, or glass flow meter, for example.

Although only one exemplary embodiment of this invention has been described in detail above, those skilled in the art will readily appreciate that many modifications are possible in the exemplary embodiment without materially departing from the novel teachings and advantages of this invention. In some instances, some features of the invention will be employed without a corresponding use of other features. Accordingly, it is appropriate that the appended claims be construed broadly and in a manner consistent with the scope of the invention.

What is claimed is:

1. An odorant system for odorizing natural gas, the system comprising:

a chamber for storing an odorant;

a wick disposed within the chamber;

a conduit connected with the chamber wherein the odorant is transferred by way of the wick from the chamber to a gas line when the chamber is connected to the gas line;

an inlet connected with the chamber for transferring the odorant into the chamber without having to disconnect the chamber from the gas line; and an outlet connected with the chamber for transferring excess odorant out of the chamber without having to disconnect the chamber from the gas line.

2. The system of claim 1 further including a pressurized first cylinder connected to the inlet.

3. The system of claim 2, further including a second cylinder connected to the outlet and a charcoal filter connected to the second cylinder.

4. The system of claim 3, further including a flow meter connected inline with the second cylinder.

5. The system of claim 4, further including an odorant line connected inline with the second cylinder and the flow meter.

6. The system of claim 5, further including a second odorant line connected to the first cylinder.

7. A method for transferring an odorant to an odorant chamber for odorizing a natural gas in a gas line, the method comprising:

venting the chamber to the atmosphere;

creating a pressure differential between an odorant source connected to the chamber and a receptacle connected to the chamber so that the odorant flows from the odorant source and into the chamber;

detecting that the odorant is flowing from the chamber to the receptacle;

stopping the odorant from flowing into the chamber;

closing the chamber off from the atmosphere;

providing a wick disposed within the chamber; and transferring the odorant from the chamber to the gas line by way of the wick.

8. The method of claim 7, further including filtering while venting to prevent an odor from venting to the atmosphere.

* * * * *